US007595054B2

(12) United States Patent
Liao et al.

(10) Patent No.: US 7,595,054 B2
(45) Date of Patent: Sep. 29, 2009

(54) FUSION ANTIGEN USED AS VACCINE

(75) Inventors: Chao-Wei Liao, Shin-Chu (TW); Chung-Nan Weng, Miaoli Hsien (TW); Hsiu-Kang Chang, Taipei (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 0 days.

(21) Appl. No.: 11/948,327

(22) Filed: Nov. 30, 2007

(65) Prior Publication Data

US 2008/0206271 A1 Aug. 28, 2008

Related U.S. Application Data

(63) Continuation-in-part of application No. 10/457,574, filed on Jun. 9, 2003, now Pat. No. 7,335,361.

(51) Int. Cl.
*A61K 39/00* (2006.01)
*A61K 39/155* (2006.01)

(52) U.S. Cl. ............... 424/192.1; 424/186.1; 424/211.1

(58) Field of Classification Search ....................... None
See application file for complete search history.

(56) References Cited

U.S. PATENT DOCUMENTS

| | | | | |
|---|---|---|---|---|
| 5,854,044 | A * | 12/1998 | Pastan et al. | 435/194 |
| 7,465,455 | B2 * | 12/2008 | Chang et al. | 424/204.1 |
| 2004/0247617 | A1 * | 12/2004 | Liao et al. | 424/192.1 |

FOREIGN PATENT DOCUMENTS

| | | | |
|---|---|---|---|
| WO | WO 00/53787 | * | 9/2000 |

OTHER PUBLICATIONS

Wang et al., "Suppression of porcine reproductive and respiratory syndrome virus replication in MARC-145 cells by shRNA targeting ORF1 region," Virus genes, vol. 35, No. 3 / Dec. 2007 (http://www.springerlink.com/content/552578245818208k/, captured on Apr. 18, 2008).

Meulenberg et al., "The molecular biology of arteriviruses," Journal of General Virology, vol. 79, 961-979 (1998).

Kim, Dal-Young, "The Application of a PRRSV Reverse Genetic System for the Study of Nonstructural Protein (NSP) Function," Ph.D. Dissertation, Department of Diagnostic Medicine/Pathobiology College of Veterinary Medicine, Kansas State University, Manhattan, Kansas (2007).

Gojobori et al., "The Origin and Evolution of Porcine Reproductive and Respiratory Syndrome Viruses," Mol. Biol. Evol. 22(4):1024-1031 (2005).

Plagemann, Peter G.W., "Porcine Reproductive and Respiratory Syndrome Virus: Origin Hypothesis," Emerging Infectious Diseases, vol. 9, No. 8 (2003).

* cited by examiner

*Primary Examiner*—Stacy B Chen
(74) *Attorney, Agent, or Firm*—Hsiu-Ming Saunders; Intellectual Property Connections, Inc.

(57) ABSTRACT

Fusion antigen used as vaccine. The invention relates to a fusion antigen specific for a target cell. The fusion antigen contains a ligand moiety, a *Pseudomonas* exotoxin A translocation domain II, an antigenic moiety, and a carboxyl terminal moiety. The ligand moiety is capable of reacting, recognizing or binding to receptors on the target cell. The carboxyl terminal moiety permits retention and processing of the fusion antigen in the endoplasmic reticulum (ER) membrane of the target cell. Pharmaceutical compositions and methods of inducing an immune response using the same are also disclosed.

42 Claims, 5 Drawing Sheets pPE-M12-K13 plasmid containing a corona-like domain (nsp11)
located in PRRSV orf1b gene M12 = the corona-like domain of PRRSV nsp11

10805       PRRSV ORF1b sub-cloned fragment       11297

DV (AatII site)-3605 a.a. of PRRS sequence
DVNNKECTVAQALGNGDKFRATDKRVVDSLRAICADLEGSSSPLPKVA        3650
HNLGFYFSPDLTQFAKLPIELAPHWPVVSTQNNEKWPDRLVASLRPLDKY        3700
SRACIGAGYMVGPSVFLGTPGVVSYYLTKFVKGEAQVLPETVFSTGRIEV        3750
DCREYLDDREREVAASLPHEFLEYLKKDELRVELKDEL    3769 a.a. –EF (EcoR1 side)-LE (Xho1)-
                                                       -YL-K13

FIG. 1A

SEQ ID NO. 1

*AspVal*AsnAsnLys GluCysThrValAla GlnAlaLeuGlyAsn GlyAspLysPheArg

AlaThrAspLysArg ValValAspSerLeu ArgAlaIleCysAla AspLeuGluGlySer

SerSerProLeuPro LysValAlaHisAsn LeuGlyPheTyrPhe SerProAspLeuThr

GlnPheAlaLysLeu ProIleGluLeuAla ProHisTrpProVal ValSerThrGlnAsn

AsnGluLysTrpPro AspArgLeuValAla SerLeuArgProLeu AspLysTyrSerArg

AlaCysIleGlyAla GlyTyrMetValGly ProSerValPheLeu GlyThrProGlyVal

ValSerTyrTyrLeu ThrLysPheValLys GlyGluAlaGlnVal LeuProGluThrVal

PheSerThrGlyArg IleGluValAspCys ArgGluTyrLeuAsp AspArgGluArgGlu

ValAlaAlaSerLeu ProHis*GluPheLeu GluTyrLeu*<u>LysLys AspGluLeuArgVal</u>

<u>GluLeuLysAspGlu Leu</u>

FIG. 1B

SEQ ID NO. 2

PE-M12-K13

The sequence of M12-K13 DNA fragment

<u>GAC GTC</u> AAT AAC AAA GAA TGC ACG GTT GCT CAG GCT CTG GGC AAC GGG GAT AAA TTT
  *Aat II*
CGT GCC ACA GAC AAG CGT GTT GTA GAT TCT CTC CGC GCC ATT TGT GCT GAT CTG GAA
GGG TCG AGC TCT CCG CTC CCG AAG GTC GCA CAC AAC TTG GGT TTT TAT TTT TCA CCT
GAC TTG ACA CAG TTT GCC AAA CTC CCA ATA GAA CTT GAC CCA CAC TGG CCG GTG GTG
TC AAC C CAG AAC AAT GAA AAG TGG CCG GAT CGT CTG GTT GCC AGC CTT CGC CCT CTC
GAC AAA TAC AGC CGC GCG TGC ATC GGT GCC GGC TAT ATG GTG GGC CCT TCG GTG TTT
CTG GGC ACT CCA GGG GTC GTG TCA TAC TAT CTC ACA AAG TTT GTT AAG GGC GAG GCT
CAA GTG CTT CCG GAA ACG TCT TCA GTA CCG GCC GAA TTG AGG TAG ACT GCC GTG AA

TAT CTT GAT GAT CGT GAG CGA GAA GTT GCT GCG TCC CTC CCA CAC <u>GAA TTC CTC GAG</u>
                                                                                                             *EcoR1*   *Xho1*
TAC CTC <u>AAA AAA GAC GAA CTG CGT GTA GAA CTG AAA GAC GAA CTG</u> TAA
           *K13*

PRRS
nsp 10
(C-terminal
domain
sequence)
and
nsp 11
(N-terminal
domain
sequence)
= M12

FIG.

```
                        SEQUENCE LISTING

<160> NUMBER OF SEQ ID NOS: 25

<210> SEQ ID NO 1
<211> LENGTH: 186
<212> TYPE: PRT
<213> ORGANISM: Artificial Sequence
<220> FEATURE:
<223> OTHER INFORMATION: PRRSV ORF1b M12 domain
      (partial Nsp10 and Nsp11) plus K13

<400> SEQUENCE: 1

Asp Val Asn Asn Lys Glu Cys Thr Val Ala Gln Ala Leu Gly Asn Gly
1               5                   10                  15

Asp Lys Phe Arg Ala Thr Asp Lys Arg Val Val Asp Ser Leu Arg Ala
            20                  25                  30

Ile Cys Ala Asp Leu Glu Gly Ser Ser Ser Pro Leu Pro Lys Val Ala
        35                  40                  45

His Asn Leu Gly Phe Tyr Phe Ser Pro Asp Leu Thr Gln Phe Ala Lys
    50                  55                  60

Leu Pro Ile Glu Leu Ala Pro His Trp Pro Val Val Ser Thr Gln Asn
65                  70                  75                  80

Asn Glu Lys Trp Pro Asp Arg Leu Val Ala Ser Leu Arg Pro Leu Asp
                85                  90                  95

Lys Tyr Ser Arg Ala Cys Ile Gly Ala Gly Tyr Met Val Gly Pro Ser
            100                 105                 110

Val Phe Leu Gly Thr Pro Gly Val Val Ser Tyr Tyr Leu Thr Lys Phe
        115                 120                 125

Val Lys Gly Glu Ala Gln Val Leu Pro Glu Thr Val Phe Ser Thr Gly
    130                 135                 140

Arg Ile Glu Val Asp Cys Arg Glu Tyr Leu Asp Asp Arg Glu Arg Glu
145                 150                 155                 160

Val Ala Ala Ser Leu Pro His Glu Phe Leu Glu Tyr Leu Lys Lys Asp
                165                 170                 175
```

Glu Leu Arg Val Glu Leu Lys Asp Glu Leu
180                 185

<210> SEQ ID NO 2
<211> LENGTH: 549
<212> TYPE: DNA
<213> ORGANISM: Artificial Sequence
<220> FEATURE:
<223> OTHER INFORMATION: PRRSV ORF1b M12 domain
      (partial Nsp10 and Nsp11) plus K13

<400> SEQUENCE: 2
gacgtcaata acaaagaatg cacggttgct caggctctgg gcaacgggga taaatttcgt      60
gccacagaca agcgtgttgt agattctctc cgcgccattt gtgctgatct ggaagggtcg     120
agctctccgc tcccgaaggt cgcacacaac ttgggttttt attttcacc tgacttgaca      180 cagtttgcca aactcccaat agaacttgac ccacactggc cggtggtgtc aacccagaac     240
aatgaaaagt ggccggatcg tctggttgcc agccttcgcc ctctcgacaa atacagccgc     300
gcgtgcatcg gtgccggcta tatggtgggc ccttcggtgt ttctgggcac tccaggggtc     360
gtgtcatact atctcacaaa gtttgttaag ggcgaggctc aagtgcttcc ggaaacggtc     420
ttcagtaccg gccgaattga ggtagactgc cgtgaatatc ttgatgatcg tgagcgagaa     480
gttgctgcgt ccctcccaca cgaattcctc gagtacctca aaaagacga actgcgtgta      540 gaactgaaa                                                              549

<210> SEQ ID NO 3
<211> LENGTH: 21
<212> TYPE: DNA
<213> ORGANISM: Artificial Sequence
<220> FEATURE:
<223> OTHER INFORMATION: Forward primer for RT-PCR detection of PRRSV in
      blood sample

<400> SEQUENCE: 3
ccagccagtc aatcagctgt g                                                21

<210> SEQ ID NO 4
<211> LENGTH: 15
<212> TYPE: DNA
<213> ORGANISM: Artificial Sequence
<220> FEATURE:
<223> OTHER INFORMATION: Reverse primer for RT-PCR detection of PRRSV in
      blood sample

<400> SEQUENCE: 4
gcggatcagg cgcac                                                       15

<210> SEQ ID NO 5
<211> LENGTH: 12
<212> TYPE: PRT
<213> ORGANISM: Artificial Sequence
<220> FEATURE:
<223> OTHER INFORMATION: a carboxyl terminal moiety sequence of the
      PRRSV fusion antigens in Examples

<400> SEQUENCE: 5

Lys Lys Asp Leu Arg Val Glu Leu Lys Asp Glu Leu
1               5                   10

<210> SEQ ID NO 6
<211> LENGTH: 13
<212> TYPE: PRT

```
<213> ORGANISM: Artificial Sequence
<220> FEATURE:
<223> OTHER INFORMATION: a carboxyl terminal moiety sequence of the
      PRRSV fusion antigens in Examples

<400> SEQUENCE: 6

Lys Lys Asp Glu Leu Arg Asp Glu Leu Lys Asp Glu Leu
1               5                   10

<210> SEQ ID NO 7
<211> LENGTH: 13
<212> TYPE: PRT
<213> ORGANISM: Artificial Sequence
<220> FEATURE:
<223> OTHER INFORMATION: a carboxyl terminal moiety sequence of the
      PRRSV fusion antigens in Examples

<400> SEQUENCE: 7

Lys Lys Asp Glu Leu Arg Val Glu Leu Lys Asp Glu Leu
1               5                   10

<210> SEQ ID NO 8
<211> LENGTH: 39
<212> TYPE: DNA
<213> ORGANISM: Artificial Sequence
<220> FEATURE:
<223> OTHER INFORMATION: a carboxyl terminal moiety sequence of the
      PRRSV fusion antigens in Examples

<400> SEQUENCE: 8
aaaaaagacg aactgagaga tgaactgaaa gacgaactg                          39

<210> SEQ ID NO 9
<211> LENGTH: 4
<212> TYPE: PRT
<213> ORGANISM: Artificial Sequence
<220> FEATURE:
<223> OTHER INFORMATION: a carboxyl terminal moiety sequence of the
      PRRSV fusion antigens in Examples

<400> SEQUENCE: 9

Lys Asp Glu Leu
1

<210> SEQ ID NO 10
<211> LENGTH: 48
<212> TYPE: DNA
<213> ORGANISM: Artificial Sequence
<220> FEATURE:
<223> OTHER INFORMATION: Forward primer M12-F1

<400> SEQUENCE: 10
tggccggtgg tgtcaaccca gaacaatgaa aagtggccgg atcgtctg                48

<210> SEQ ID NO 11
<211> LENGTH: 51
<212> TYPE: DNA
<213> ORGANISM: Artificial Sequence
<220> FEATURE:
<223> OTHER INFORMATION: Forward primer M12-F2

<400> SEQUENCE: 11
cagtttgcca aactcccaat agaacttgca ccacactggc cggtggtgtc a            51

<210> SEQ ID NO 12
<211> LENGTH: 48
<212> TYPE: DNA
```

```
<213> ORGANISM: Artificial Sequence
<220> FEATURE:
<223> OTHER INFORMATION: Forward primer M12-F3

<400> SEQUENCE: 12
aacttgggtt tttatttttc acctgacttg acacagtttg ccaaactc                48

<210> SEQ ID NO 13
<211> LENGTH: 48
<212> TYPE: DNA
<213> ORGANISM: Artificial Sequence
<220> FEATURE:
<223> OTHER INFORMATION: Forward primer M12-F4

<400> SEQUENCE: 13
gggtcgagct ctccgctccc gaaggtcgca cacaacttgg gttttat                 48

<210> SEQ ID NO 14
<211> LENGTH: 45
<212> TYPE: DNA
<213> ORGANISM: Artificial Sequence
<220> FEATURE:
<223> OTHER INFORMATION: Forward primer M12-F5

<400> SEQUENCE: 14
tctctccgcg ccatttgtgc tgatctggaa gggtcgagct ctccg                   45

<210> SEQ ID NO 15
<211> LENGTH: 51
<212> TYPE: DNA
<213> ORGANISM: Artificial Sequence
<220> FEATURE:
<223> OTHER INFORMATION: Forward primer M12-F6

<400> SEQUENCE: 15
gataaatttc gtgccacaga caagcgtgtt gtagattctc tccgcgccat t            51

<210> SEQ ID NO 16
<211> LENGTH: 42
<212> TYPE: DNA
<213> ORGANISM: Artificial Sequence
<220> FEATURE:
<223> OTHER INFORMATION: Forward primer M12-F7

<400> SEQUENCE: 16
acggttgctc aggctctggg caacggggat aaatttcgtg cc                      42

<210> SEQ ID NO 17
<211> LENGTH: 42
<212> TYPE: DNA
<213> ORGANISM: Artificial Sequence
<220> FEATURE:
<223> OTHER INFORMATION: Forward primer M12-F8

<400> SEQUENCE: 17 cccccccgacg tcaataacaa agaatgcacg gttgctcagg ct                     42

<210> SEQ ID NO 18
<211> LENGTH: 51
<212> TYPE: DNA
<213> ORGANISM: Artificial Sequence
<220> FEATURE:
<223> OTHER INFORMATION: Reverse primer M12-R1

<400> SEQUENCE: 18
gcggctgtat ttgtcgagag ggcgaaggct ggcaaccaga cgatccggcc a            51
```

<210> SEQ ID NO 19
<211> LENGTH: 48
<212> TYPE: DNA
<213> ORGANISM: Artificial Sequence
<220> FEATURE:
<223> OTHER INFORMATION: Reverse primer M12-R2

<400> SEQUENCE: 19
agggcccacc atatagccgg caccgatgca cgcgcggctg tatttgtc            48

<210> SEQ ID NO 20
<211> LENGTH: 51
<212> TYPE: DNA
<213> ORGANISM: Artificial Sequence
<220> FEATURE:
<223> OTHER INFORMATION: Reverse primer M12-R3

<400> SEQUENCE: 20
gtatgacacg acccctggag tgcccagaaa caccgaaggg cccaccatat a         51

<210> SEQ ID NO 21
<211> LENGTH: 45
<212> TYPE: DNA
<213> ORGANISM: Artificial Sequence
<220> FEATURE:
<223> OTHER INFORMATION: Reverse primer M12-R4

<400> SEQUENCE: 21
agcctcgccc ttaacaaact tgtgagata gtatgacacg acccc                 45

<210> SEQ ID NO 22
<211> LENGTH: 51
<212> TYPE: DNA
<213> ORGANISM: Artificial Sequence
<220> FEATURE:
<223> OTHER INFORMATION: Reverse primer M12-R5

<400> SEQUENCE: 22
tcggccggta ctgaagaccg tttccggaag cacttgagcc tcgcccttaa c         51

<210> SEQ ID NO 23
<211> LENGTH: 40
<212> TYPE: DNA
<213> ORGANISM: Artificial Sequence
<220> FEATURE:
<223> OTHER INFORMATION: Reverse primer M12-R6

<400> SEQUENCE: 23
gatattcacg gcagtctacc tcaattcggc cggtactgaa                      40

<210> SEQ ID NO 24
<211> LENGTH: 46
<212> TYPE: DNA
<213> ORGANISM: Artificial Sequence
<220> FEATURE:
<223> OTHER INFORMATION: Reverse primer M12-R7

<400> SEQUENCE: 24
acgcagcaac ttctcgctca cgatcatcaa gatattcacg gcagtc               46

<210> SEQ ID NO 25
<211> LENGTH: 45
<212> TYPE: DNA
<213> ORGANISM: Artificial Sequence
<220> FEATURE:

-continued

```
<223> OTHER INFORMATION: Reverse primer M12-R8

<400> SEQUENCE: 25 tttttctcg aggaattcgt gtgggaggga cgcagcaact tctcg           45
```

FUSION ANTIGEN USED AS VACCINE

CROSS-REFERENCE TO RELATED PATENT APPLICATION

This application is a continuation-in-part application, and claims benefit of U.S. patent application Ser. No. 10/457,574 filed Jun. 9, 2003, which status is issued as U.S. Pat. No. 7,335,361 issue date on Feb. 26, 2008, entitled "Fusion antigen used as vaccine," by Chao-Wei Liao and Chung-Nan Weng, the disclosure of which is hereby incorporated herein in its entirety by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The invention relates to a fusion antigen. More particularly, the invention relates to a fusion antigen used as a T-cell vaccine.

BACKGROUND OF THE INVENTION

Cell-mediated immune reactions depend on direct interactions between T-lymphocytes and cells bearing the antigen that T-cells recognize. T cells recognize body cells infected with viruses, which replicate inside cells using the synthetic machinery of the cell itself. Antigens derived from the replication of a virus, however, are present on the surface of infected cells (by MHC class I), where they are recognized by cytotoxic T-cells (CD8+ T-cells), which may then control the infection by killing the cells before the virus replication is complete.

Vaccines for prophylaxis of viral infections are usually live attenuated organisms with reduced pathogenicity that would stimulate protective immunity. Foreign proteins of a live virus that is used as a live attenuated vaccine are recognized and processed in the endoplasmic reticulum (ER) lumen of antigen presenting cells (APCs) when the virus replicates to form an endogenous processing peptide. The process includes antigen modification and proper digestion. However, a live attenuated vaccine, especially in RNA virus, has a quite strong tendency to recover toxicity and virulence. For example, the toxicity of an infectious laryngotracheitis virus (ILTV) recovers both in vaccine or attenuated strains. Besides, multiple passages of a virus should be operated. Therefore, the ability to evoke an immune response is discredited. It is a time-consuming job to develop a live attenuated vaccine.

To prevent the recovery of a live attenuated vaccine, gene deficient vaccines are developed, such as Aujeszky's disease vaccines, gI negative vaccines, and PRV marker vaccines.

Viruses or bacteria of vaccina or fowlpox are used as vectors for carrying the genes of antigens. Through recombinant DNA technology, the time for development of a good vaccine is reduced and multiple serotypes of vaccine can be achieved at the same time. Examples of such vaccines are fowlpoxvirus and *Salmonella* vector systems and Syntro Vet (US) gene recombinant vaccines. On the other hand, when a microorganism, especially an RNA virus, is used as a vector vaccine, the microorganism would derive a new species or a new strain. The safety of such vector vaccines is again challenged. In addition, traditional recombinant subunit vaccines are usually helpless in triggering a cell-mediated immune response. They are exogenous antigens, which are taken into macrophages, dendritic cells and B lymphocytes. Peptides of immunogen epitopes from exogenous antigens are generated after internalization of antigens by APCs via fluid phase pinocytosis or membrane-bound receptors. The peptides are then generated in the endosomal compartments of the APCs and sorted by empty MHC class II molecules to form peptide-MHC class II complexes based on the affinities between MHC class II molecules and peptides. The peptide-MHC class II complexes are then translocated to the surface of the APCs, where they are recognized by CD4+ T-cells. However, subunit type proteins recognized by CD8+ T-cells cannot be used efficiently as vaccines because once administration, they are internalized in endosomal compartments, where they are likely to be either extensively degraded or fail to interact with the MHC class I pathway. Furthermore, CD4+ cells (Th cells) can activate both humoral immunity and cell-mediated immune response by Th1 and Th2 helper T-cells, respectively. Th1 and Th2 cells regulate each other for the balance of humoral immunity and cell-mediated immune response.

Viruses that infect immunological cells such as T-cell, B-cell, dendritic cell, monocyte, or macrophage have been discovered and investigated. Examples of such swine infected viruses are porcine reproductive and respiratory syndrome virus, circovirus type II, and human infected virus, human immunodeficiency virus. Such viruses shut down the ability of recognition of foreign proteins as antigens in the antigen presenting cells. The immunological cells cannot evoke an immunization response and carry the viruses. The animals that have been infected by these types of viruses are easily secondarily infected by other pathogens. It is a pity that a useful vaccine targeting virus-infected immunological cells is still lacking.

In particular, porcine reproductive and respiratory syndrome virus (PRRSV) results in high losses in animal husbandry every year. The virus infects macrophages (in the alveolar and spleen), brain microglia and monocytes, and exists in the blood and organs of the infected animals. Antibodies have little effect on the virus and even stimulate mutations of the virus. In the mechanism of antibody dependent enhancement (ADE), the use of antibodies leads to more severe infections. About 50 to 80% of pigs are infected by such virus. Generally, the animals infected by the virus have no significant symptoms, but the immunity of the infected animals is reduced. This leads to a decrease of weight gain and an increase in the death rate due to the secondary infection. PRRSV is an RNA virus. Not only swine but ducks can be infected by PRRSV as well. A live attenuated vaccine against PRRSV was developed. However, mutation of the viruses in the live vaccine often occurs. Fortunately, recent reports of HIV vaccine development strongly indicate that cytotoxic T-cells (CTLs) are essential for controlling HIV infection. (Hanne G-S et al 2000, Journal of virology, vol. 74, No. 4. p. 1694-1703). To develop a safe and effective PRRS vaccine is urgently desired.

Therefore, a heretofore unaddressed need exists in the art to address the aforementioned deficiencies and inadequacies, especially in connection with development of T-cell vaccines against virus infection.

SUMMARY OF THE INVENTION

In one aspect, the invention relates to a fusion antigen specific for a target cell, in which the fusion antigen contains: (a) an antigenic moiety; (b) a ligand moiety that is capable of reacting, recognizing or binding to a receptor on the target cell; (c) a *Pseudomonas* exotoxin A translocation domain II; and (d) a carboxyl terminal moiety that includes a polypeptide that has an amino acid sequence KDEL. The carboxyl terminal moiety is connected to the antigenic moiety via a bridge region.

In one embodiment of the invention, the carboxyl terminal moiety includes a polypeptide that has an amino acid sequence KKDELRXELKDEL, in which X is V or D.

The antigenic moiety is derived from porcine reproductive and respiratory syndrome virus, circovirus type II, or human immunodeficiency virus.

In one embodiment of the invention, the antigenic moiety is derived from a pathogen selected from the group consisting of arterivirus, torovirus, and coronavirus.

In another embodiment of the invention, the antigenic moiety is derived from a pathogen selected from the group consisting of equine arteritis virus, porcine reproductive and respiratory syndrome virus, lactate dehydrogenase elevating virus, and simian hemorrhagic fever virus.

In one embodiment of the invention, the antigenic moiety is derived from porcine reproductive and respiratory syndrome virus (PRRSV) ORF1b or ORF7.

In another embodiment of the invention, the antigenic moiety is derived from porcine reproductive and respiratory syndrome virus (PRRSV) Nsp10 and Nsp11.

In another embodiment of the invention, the antigenic moiety includes a polypeptide that has an amino acid sequence set forth by SEQ ID NO: 1.

Yet in another embodiment of the invention, the antigenic moiety includes a polypeptide that is a translation product of a DNA fragment having a nucleotide sequence set forth by SEQ ID NO: 2.

In one embodiment, the ligand moiety is a *Pseudomonas* exotoxin A binding domain I.

In another aspect, the invention relates to a pharmaceutical composition including one or more than one fusion antigen as aforementioned, and a pharmaceutically acceptable carrier.

In one embodiment of the invention, the pharmaceutical composition includes at least one fusion antigen that has an antigenic moiety derived from porcine reproductive and respiratory syndrome virus (PRRSV) ORF1b. Optionally, the composition may further include at least one fusion antigen that has an antigenic moiety derived from porcine reproductive and respiratory syndrome virus (PRRSV) ORF7.

In another embodiment of the invention, the pharmaceutical composition includes at least one fusion antigen that has an antigenic moiety derived from porcine reproductive and respiratory syndrome virus (PRRSV) ORF7.

In one embodiment of the invention, the pharmaceutical composition includes more than one fusion antigen, in which at least one fusion antigen has an antigenic moiety derived from porcine reproductive and respiratory syndrome virus (PRRSV) ORF1b.

In another embodiment, the pharmaceutical composition includes more than one fusion antigen, in which at least one fusion antigen has an antigenic moiety derived from porcine reproductive and respiratory syndrome virus (PRRSV) ORF7.

Yet in another aspect, the invention relates to a method of inducing an immune response in an animal against a pathogen infection. The method includes the steps of: (a) providing a pharmaceutical composition; and (b) inoculating the fusion antigen into the animal.

In one embodiment of the invention, the step (a) provides a pharmaceutical composition that includes one or more than one fusion antigen, and a pharmaceutically acceptable carrier. The fusion antigen contains an antigen moiety, a ligand moiety and a *Pseudomonas* exotoxin A translocation domain II, and a carboxyl terminal moiety that includes a polypeptide having an amino acid sequence KDEL. The immune response is directed against the pathogen from which the antigen moiety is derived.

In one embodiment of the invention, the step (a) provides a pharmaceutical composition that includes at least one fusion antigen having an antigenic moiety derived from porcine reproductive and respiratory syndrome virus (PRRSV) ORF1b.

In another embodiment of the invention, the step (a) provides a pharmaceutical composition that includes: (a) at least one fusion antigen having an antigenic moiety derived from porcine reproductive and respiratory syndrome virus (PRRSV) ORF1b; and (b) at least one fusion antigen having an antigenic moiety derived from porcine reproductive and respiratory syndrome virus (PRRSV) ORF7.

In one embodiment of the invention, the step (a) provides a pharmaceutical composition that includes one or more than one fusion antigen, and a pharmaceutically acceptable carrier. The fusion antigen contains an antigen moiety, a ligand moiety and a *Pseudomonas* exotoxin A translocation domain II, and a carboxyl terminal moiety that includes a polypeptide having an amino acid sequence KKDELRXELKDEL, in which X is V or D. Likewise, the pharmaceutical composition herein may includes at least one fusion antigen that has an antigenic moiety derived from porcine reproductive and respiratory syndrome virus (PRRSV) ORF1b. Alternatively, the pharmaceutical composition herein may include: (a) at least one fusion antigen having an antigenic moiety derived from porcine reproductive and respiratory syndrome virus (PRRSV) ORF1b; and (b) at least one fusion antigen having an antigenic moiety derived from porcine reproductive and respiratory syndrome virus (PRRSV) ORF7.

In one embodiment of the invention, the aforementioned method induces an immune response directed against a pathogen that is a member selected from the group consisting of porcine reproductive and respiratory syndrome virus, circovirus type II, or human immunodeficiency virus.

In another embodiment of the invention, the aforementioned method induces an immune response directed against a pathogen that is a member selected from the group consisting of equine arteritis virus (EAV), porcine reproductive and respiratory syndrome virus (PRRSV), lactate dehydrogenase elevating virus (LDV), and simian hemorrhagic fever virus (SHFV).

In another embodiment of the invention, the aforementioned method induces an immune response directed against a pathogen that is a member selected from the group consisting of arterivirus, torovirus, and coronavirus.

In one embodiment of the invention, the aforementioned step (a) provides a pharmaceutical composition that includes one or more than one fusion antigen as aforementioned. The fusion antigen herein is specific for a target cell. The target cell may be an antigen presenting cell. It may be selected from T-cells, B-cells, dendritic cells, monocytes, or macrophages.

BRIEF DESCRIPTION OF THE DRAWINGS

FIG. 1A illustrates the PRRSV ORF 1b sub-cloned fragment Nsp 11 (nucleotide 1080~nucleotide 11297, top panel) and the corresponding amino acid sequence of protein fragment Nsp 10 and Nsp 11 plus K13 in one letter code (bottom panel: SEQ ID NO: 1).

FIG. 1B illustrates the corresponding 3 letter amino acid sequence of the protein fragment in FIG. 1A (SEQ ID NO: 1).

FIG. 2 illustrates the nucleotide sequence of M12-K13 DNA fragment (SEQ ID NO: 2).

DETAILED DESCRIPTION OF THE INVENTION

Definitions

Figure 3:
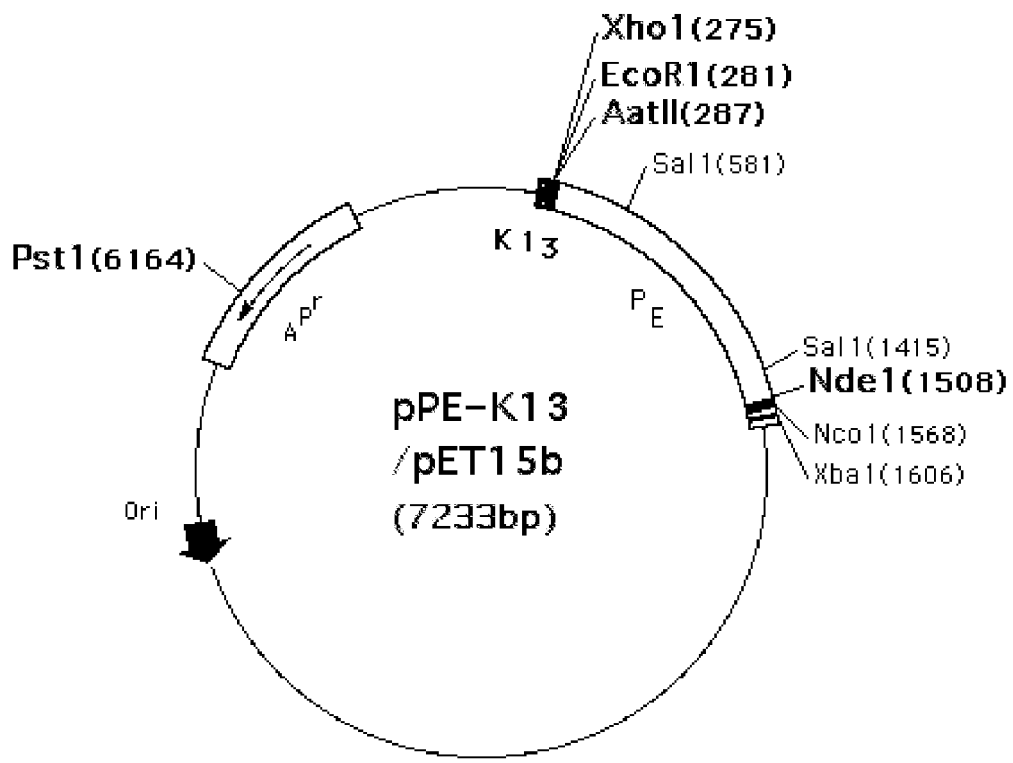
FIG. 3 illustrates the plasmid pPE-K13 map, in which PE represents PE(ΔIII).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The invention provides a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the endoplasmic reticulum (ER) membrane of the target cell.

As used herein, the term "fusion antigen" refers to a recombinant protein which can evoke an immune response in an animal. Preferably, the fusion antigen comprises epitopes for evoking an immune response directly and other portions for enhancing an immune response such as mediating delivery, transporting, processing, and expressing or for equipment of multiple functions.

Preferably, the target cell is an antigen presenting cell. More preferably, the target cell is selected from the group consisting of T-cells, B-cells, dendritic cells, monocytes, and macrophages.

As used herein, the term "an antigenic moiety" refers to a peptide fragment that can evoke an immune response. In one embodiment of the invention, the antigenic moiety is an epitope. According to the invention, the antigenic moiety is a protein of a pathogenic species, which can highly activate an immune response. Such proteins comprise, for example, but are not limited to, coat proteins, nucleoproteins or cell membrane proteins. The antigenic moiety can be a peptide cloned directly from the pathogenic species as well as a recombinant protein modified by artisans skilled in the field for enhancing the ability to evoke an immune response, for being manufactured more conveniently and for being delivered more easily. Preferably, the antigenic moiety is derived from porcine reproductive and respiratory syndrome virus (PRRSV), Circovirus type II, or human immunodeficiency virus. Preferably, the antigenic moiety may be PRRSV ORF1, 1b, 2, 3, 4, 5, 6, or 7. In one more preferred embodiment of the invention, the antigenic moiety is PRRSV ORF1b, or M12 corona-like domain. For evoking a more severe immune response, the antigenic moiety comprises at least one antigenic unit and the adjacent antigenic unit is connected by a bridge region. According to the invention, the bridge region may be a small fragment of peptide that evokes little immune response to prevent the immune system from recognizing it.

As used herein, the term "ligand moiety" refers generally to all molecules which are capable of reacting, recognizing or binding to the receptor on a target cell. Examples of such receptors include, but are not limited to, antibody receptors, growth factor receptors, lymphokine receptors, cytokine receptors, hormone receptors and the like. In some embodiments of the invention, the receptor for binding to the ligand moiety is selected from the group consisting of TGFα receptors, IL2 receptors, IL4 receptors, IL6 receptors, IGF1 receptors, CD4 receptors, IL18 receptors, IL 12 receptors, EGF receptors, LDL receptors and α2-macroglobulin receptors. The ligand moiety has an ability of binding to the cell membrane of the target cell for anchoring the fusion antigen to the target cell. The immune system is initiated by the fusion antigen's binding to the receptors on the target cell. Preferably, the ligand moiety is a *Pseudomonas* exotoxin A binding domain I. *Pseudomonas* exotoxin A (PE) is a single polypeptide chain of 613 amino acids. X-ray crystallographic studies and mutational analysis of the PE molecule show that PE consists of three domains: an amino terminal cell receptor binding domain (Domain I); a middle translocation domain (Domain II); and a carboxyl terminal activity domain (Domain III) (see U.S. Pat. No. 5,705,163, which is incorporated into references).

As used herein, the term "*Pseudomonas* exotoxin A binding domain I" refers to a peptide fragment that has the same sequence as the amino terminal cell receptor binding domain of *Pseudomonas* exotoxin A or a functionally equivalent fragment. The amino terminal cell receptor binding domain of

*Pseudomonas* exotoxin A comprises two sub-domains, designated as domain Ia and domain Ib. The configuration of domain Ia and domain Ib can bind to a LDL receptor or α2-macroglobulin receptor on a cell surface.

As used herein, the term "*Pseudomonas* exotoxin A binding domain II" refers to a peptide fragment that has the same sequence as the middle translocation domain of *Pseudomonas* exotoxin A or a functionally equivalent fragment. The *Pseudomonas* exotoxin A translocation domain II has an ability to translocate the fusion antigen into the cytoplasm of the target cell. The fusion antigen is translocated into the target cell after attaching to the target cell membrane.

As used herein, the term "carboxyl terminal moiety which permits retention of the fusion antigen to the endoplasmic reticulum (ER) membrane of a target cell" refers to a peptide fragment that enables the fusion antigen to bind to the ER membrane and to retain it in the ER lumen for glycosylation and make it appears to be more like foreign protein. In one embodiment of the invention, the carboxyl terminal moiety comprises, in a direction from the amino terminus to the carboxyl terminus, the following amino acid residues:

$R^1$—$R^2$—$R^3$—$R^4$—$(R^5)_n$

Wherein, $R^1$ is a positively charged amino acid residue;
$R^2$ is a negatively charged amino acid residue;
$R^3$ is a negatively charged amino acid residue;
$R^4$ is L;
$R^5$ is a positively charged amino acid residue; and
n is 0 or 1.

Preferably, the carboxyl terminal moiety is a member of the KDEL family protein. As used herein, the term "KDEL family protein" refers to a group of proteins, which has a similar carboxyl end binding to the ER membrane of a cell and further has an ability for retention of such protein in the ER lumen. Generally, the length of the carboxyl end ranges from 4 to 16 residues. As discussed in U.S. Pat. No. 5,705,163 (which is incorporated into the references), the amino residues at the carboxyl end of a KDEL family protein, particularly those in the last five amino acids, are important. As shown in the studies on the similar sequences present in different molecules and performing a specific biological function, a sequence that retains a newly formed protein within the endoplasmic reticulum is Lys Asp Glu Leu (KDEL) (SEQ ID NO: 9). These findings suggest that the sequence at the carboxyl end of the fusion antigen according to the invention acts as some type of recognition sequence to assist translocation of the fusion antigen from an endocytic compartment into the ER and retains it in the lumen. In a preferred embodiment, the carboxyl terminal moiety comprises a sequence of KDEL (SEQ ID NO: 9). In a more preferred embodiment, the carboxyl terminal moiety comprises a sequence of KKDL-RDEL-KDEL (SEQ ID NO: 5), KKDELRDELKDEL (SEQ ID NO: 6), or KKDEL-RVELKDEL (SEQ ID NO: 7), or KKDEL-RXEL-KDEL, in which R is D or V.

The invention is characterized by the design of carboxyl terminal moiety, which enables the fusion antigen to be processed in the ER of the target cell for combining with MHC class I molecules and being recognized by T-cells. The fusion antigen according to the invention is useful in triggering cell-mediated immune reactions.

According to the invention, the fusion antigen is used for the immunization of animals. One objective of the invention is to provide a pharmaceutical composition comprising the fusion antigen of the invention together with a pharmaceutical acceptable carrier. Preferably, the pharmaceutical composition is a T-cell vaccine.

As used herein, the term "T-cell vaccine" refers to a vaccine that can protect a subject from infection by activating cell-mediated immune response. The crucial role of the T-cell vaccine is cytotoxic T-cell (also known as cytotoxic T lymphocyte, CD8$^+$T-cell, and CTL) and memory T-cells ($T_{cm}$ and $T_{em}$).

The present invention also provides a method of immunizing an animal comprising the steps of:

(a) providing a fusion antigen specific for a target cell comprising an antigenic moiety, a ligand moiety which is capable of reacting, recognizing or binding to a receptor on the target cell, a *Pseudomonas* exotoxin A translocation domain II, and a carboxyl terminal moiety which permits retention of the fusion antigen in the endoplasmic reticulum (ER) membrane of the target cell; and (b) inoculating the animal with the fusion antigen.

In the Step (b) of the method, the animals may be inoculated with the fusion antigen in any way known to artisans skilled in this field. For example, the fusion antigen may be delivered by injection or in a form of oral vaccine. Booster shots are optional, if necessary. Preferably, the inoculation is performed before infection. Newly born animals, even an embryo, may also be inoculated with the fusion antigen to produce better immunity.

According to the invention, the following actions occur during the process of the response to the immunization:

(c) the target cell membrane binds to the ligand moiety for anchoring the fusion antigen to the target cell;

(d) the fusion antigen is translocated into the cytoplasm of the target cell by the *Pseudomonas* exotoxin A translocation domain II;

(e) the ER membrane of the target cell binds to the carboxyl terminal moiety of the fusion antigen for retention of the fusion antigen in the ER lumen;

(f) the antigenic moiety is processed in the ER lumen;

(g) the processed antigenic moiety binds with a MHC class I molecule;

(h) the processed antigenic moiety is carried by the MHC Class I molecule to the target cell surface;

(i) the processed antigenic moiety carried by the MHC class I molecule is recognized by CD8+ T-cell to obtain an immune message; and (j) the immune message is stored by memory T-cells for immunizing the animal.

In Action (c), the ligand moiety of the fusion antigen leads the fusion antigen to bind to the receptors on the target cell membrane for anchoring the fusion antigen to the target cell.

In Action (d), the fusion antigen is translocated into the cytoplasm of the target cell by the *Pseudomonas* exotoxin A translocation domain II. The translocation leads the fusion antigen to entry into the target cell.

In Action (e), the carboxyl terminal moiety of the fusion antigen binds to the ER membrane of the target cell for retention of the fusion antigen in the ER lumen for the process of the fusion antigen.

In Action (f), the antigenic moiety is processed in the ER lumen. The process includes, but is not limited to, antigen modification such as glycosilation and proper digestion by enzyme in the ER lumen.

In Action (g), the processed fusion antigen can bind to a MHC class I molecule. The MHC class I molecule itself is an uncompleted folding protein and binds to many chaperones. The processed fusion antigen binds to the peptide-binding cleft to complete folding and stimulates the release of the chaperones.

In Action (h), the processed antigenic moiety is presented to the target cell surface by the MHC class I molecule. The folded MHC class I and processed antigenic moiety is delivered to the cell surface.

In Action (i), the processed antigenic moiety carried by the MHC class I molecule was recognized by CD8+ T-cell to obtain an immune message for the recognition of the cytotoxic T-cell and also for the storage an immune message into memory T-cells. Examples of the memory T-cells are $T_{cm}$ and $T_{em}$ cells.

In Action (j), the immune message is stored by memory T-cells for immunizing the animal. When the animal immunized with the fusion antigen is infected by the same antigen again, the memory T-cells evoke a stronger immune response in a shorter time. T-cell vaccine provides an endogenous processing antigen which can be processed in the ER lumen of the target cell.

The present invention also relates to a fusion porcine reproductive and respiratory syndrome virus (PRRSV) ORF1b or Nsp11 antigen comprising a PRRSV ORF1b partial fragment or Nsp11 moiety; a *Pseudomonas* exotoxin A binding domain I; a *Pseudomonas* exotoxin A translocation domain II; and a carboxyl terminal moiety which permits retention of the fusion antigen in the endoplasmic reticulum (ER) membrane of a target cell.

A pharmaceutical composition comprising the fusion antigen of the invention together with a pharmaceutically acceptable carrier is also provided.

Another aspect of the invention is to provide a method of immunizing an animal for the prevention of porcine reproductive and respiratory syndrome virus (PRRSV), which comprises the steps of:

(a) providing a fusion antigen comprising a PRRSV ORF1b or Nsp11 antigen moiety, a *Pseudomonas* exotoxin A binding domain I, a *Pseudomonas* exotoxin A translocation domain II, and a carboxyl terminal moiety which permits retention of the antigen in the endoplasmic reticulum (ER) membrane of an target cell; and (b) inoculating the fusion antigen into the animal.

In one aspect, the invention relates to a fusion antigen specific for a target cell, in which the fusion antigen contains: (a) an antigenic moiety; (b) a ligand moiety that is capable of reacting, recognizing or binding to a receptor on the target cell; (c) a *Pseudomonas* exotoxin A translocation domain II; and (d) a carboxyl terminal moiety that includes a polypeptide that has an amino acid sequence KDEL. The carboxyl terminal moiety is connected to the antigenic moiety via a bridge region.

In one embodiment of the invention, the carboxyl terminal moiety includes a polypeptide that has an amino acid sequence KKDELRXELKDEL, in which X is V or D.

The antigenic moiety is derived from porcine reproductive and respiratory syndrome virus, circovirus type II, or human immunodeficiency virus.

In one embodiment of the invention, the antigenic moiety is derived from a pathogen selected from the group consisting of arterivirus, torovirus, and coronavirus.

In another embodiment of the invention, the antigenic moiety is derived from a pathogen selected from the group consisting of equine arteritis virus, porcine reproductive and respiratory syndrome virus, lactate dehydrogenase elevating virus, and simian hemorrhagic fever virus.

In one embodiment of the invention, the antigenic moiety is derived from porcine reproductive and respiratory syndrome virus (PRRSV) ORF1b or ORF7.

In another embodiment of the invention, the antigenic moiety is derived from porcine reproductive and respiratory syndrome virus (PRRSV) Nsp10 and Nsp11.

In another embodiment of the invention, the antigenic moiety includes a polypeptide that has an amino acid sequence set forth by SEQ ID NO: 1.

Yet in another embodiment of the invention, the antigenic moiety includes a polypeptide that is a translation product of a DNA fragment having a nucleotide sequence set forth by SEQ ID NO: 2.

In one embodiment, the ligand moiety is a *Pseudomonas* exotoxin A binding domain I.

In another aspect, the invention relates to a pharmaceutical composition including one or more than one fusion antigen as aforementioned, and a pharmaceutically acceptable carrier.

In one embodiment of the invention, the pharmaceutical composition includes at least one fusion antigen that has an antigenic moiety derived from porcine reproductive and respiratory syndrome virus (PRRSV) ORF1b. Optionally, the composition may further include at least one fusion antigen that has an antigenic moiety derived from porcine reproductive and respiratory syndrome virus (PRRSV) ORF7.

In another embodiment of the invention, the pharmaceutical composition includes at least one fusion antigen that has an antigenic moiety derived from porcine reproductive and respiratory syndrome virus (PRRSV) ORF7.

In one embodiment of the invention, the pharmaceutical composition includes more than one fusion antigen, in which at least one fusion antigen has an antigenic moiety derived from porcine reproductive and respiratory syndrome virus (PRRSV) ORF1b.

In another embodiment, the pharmaceutical composition includes more than one fusion antigen, in which at least one fusion antigen has an antigenic moiety derived from porcine reproductive and respiratory syndrome virus (PRRSV) ORF7.

Yet in another aspect, the invention relates to a method of inducing an immune response in an animal against a pathogen infection. The method includes the steps of: (a) providing a pharmaceutical composition; and (b) inoculating the fusion antigen into the animal.

In one embodiment of the invention, the step (a) provides a pharmaceutical composition that includes one or more than one fusion antigen, and a pharmaceutically acceptable carrier. The fusion antigen contains an antigen moiety, a ligand moiety and a *Pseudomonas* exotoxin A transloction domain II, and a carboxyl terminal moiety that includes a polypeptide having an amino acid sequence KDEL. The immune response is directed against the pathogen from which the antigen moiety is derived.

In one embodiment of the invention, the step (a) provides a pharmaceutical composition that includes at least one fusion antigen having an antigenic moiety derived from porcine reproductive and respiratory syndrome virus (PRRSV) ORF1b.

In another embodiment of the invention, the step (a) provides a pharmaceutical composition that includes: (a) at least one fusion antigen having an antigenic moiety derived from porcine reproductive and respiratory syndrome virus (PRRSV) ORF1b; and (b) at least one fusion antigen having an antigenic moiety derived from porcine reproductive and respiratory syndrome virus (PRRSV) ORF7.

In one embodiment of the invention, the step (a) provides a pharmaceutical composition that includes one or more than one fusion antigen, and a pharmaceutically acceptable carrier. The fusion antigen contains an antigen moiety, a ligand moiety and a *Pseudomonas* exotoxin A transloction domain II, and a carboxyl terminal moiety that includes a polypeptide having an amino acid sequence KKDELRXELKDEL, in which X is V or D. Likewise, the pharmaceutical composition herein may includes at least one fusion antigen that has an antigenic moiety derived from porcine reproductive and respiratory syndrome virus (PRRSV) ORF1b. Alternatively, the pharmaceutical composition herein may include: (a) at least one fusion antigen having an antigenic moiety derived from porcine reproductive and respiratory syndrome virus (PRRSV) ORF1b; and (b) at least one fusion antigen having an antigenic moiety derived from porcine reproductive and respiratory syndrome virus (PRRSV) ORF7.

In one embodiment of the invention, the aforementioned method induces an immune response directed against a pathogen that is a member selected from the group consisting of porcine reproductive and respiratory syndrome virus, circovirus type II, or human immunodeficiency virus.

In another embodiment of the invention, the aforementioned method induces an immune response directed against a pathogen that is a member selected from the group consisting of equine arteritis virus (EAV), porcine reproductive and respiratory syndrome virus (PRRSV), lactate dehydrogenase elevating virus (LDV), and simian hemorrhagic fever virus (SHFV). Sequences of ORF1b and ORF7 thereof are available in the public domain. For example, sequences may be extracted from the EMBL/GenBank database (accession no. X53459 [EAV], M96262 [PRRSV], U15146 [LDV], and U63121 [SHFV].

In another embodiment of the invention, the aforementioned method induces an immune response directed against a pathogen that is a member selected from the group consisting of arterivirus, torovirus, and coronavirus.

In one embodiment of the invention, the aforementioned step (a) provides a pharmaceutical composition that includes one or more than one fusion antigen as aforementioned. The fusion antigen herein is specific for a target cell. The target cell may be an antigen presenting cell. It may be selected from T-cells, B-cells, dendritic cells, monocytes, or macrophages.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Material and Methods

Plasmid Construction pPE-M12-K13. The plasmid pPE-M12-K13 contained a corona-like domain M12 as an antigenic moiety, PE (ΔII) as a ligand moiety and a translocation moiety, and K13 as a carboxyl terminal moiety. The M12 domain sequence is located within the PRRSV ORE 1b gene. The PRRSV ORF 1b sequence was extracted from the EMBL/GenBank database accession no. M96262. The subcloned M12 fragment was derived from PRRSV Nsp 10 (C-terminal domain sequence) and Nsp 11 (N-terminal domain sequence). The antigenic moiety PRRSV M12 (or ORF 1b sub-cloned fragment) was synthesized with specific primers listed in Table 1.

Figure 4:
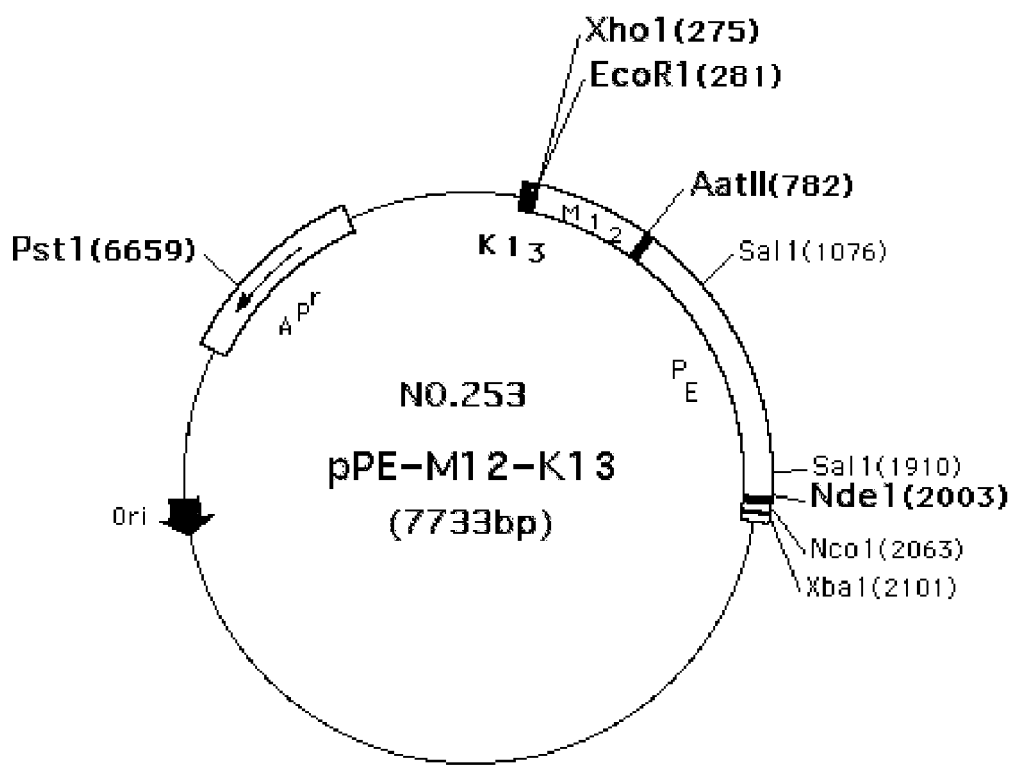
FIG. 4 illustrates the plasmid pPE-M12-K13 map, in which PE represents PE(ΔIII).

To generate the plasmid pPE-M12-K13, the PRRSV ORF 1b DNA fragment nt 10805~1297 was subcloned into the plasmid pPE-K13 by Aat II and EcoRI sites insertion. FIG. 1A shows the protein fragment of M12 plus K 13, where the restriction sites are denoted in bold letters. The corresponding 3 letter amino acid sequence of FIG. 1A protein fragment is shown in FIG. 1B (SEQ ID NO: 1), in which the K13 sequence is denoted in underlined, bold letters, and the restriction sites and a short bridge between XhoI and the K13sequence are denoted in bold, italic letters. FIG. 2 shows the nucleotide sequence (SEQ ID NO: 2) of M12-K13 DNA fragment comprising M12 (i.e., PRRS Nsp 10 plus Nsp11 gene) and K13. FIG. 3 shows the plasmid pPE-K13, and FIG. 4 shows plasmid pPE-M12-K13 comprising M12 domain (i.e., corona-like domain).

pPE-K13. The plasmid pPE-K13 contained PE (ΔIII) as a ligand moiety plus a translocation moiety, and K13 as a carboxyl terminal moiety (FIG. 3). The PE(ΔIII) (referred as PE in the FIG. 3) included a *Pseudomonas exotoxin* A binding domain I and a translocation domain II. A plasmid pPE(ΔIII) was constructed according to the method described previously in US Patent Publication No. 2004/0247617, which is incorporated herein by reference in its entirety.

The K13 carboxyl terminal moiety comprises a peptide sequence KKDELRVELKDEL (SEQ ID NO: 7), which was encoded by AAA AAAGACGAACTGAGAGA TGAACT-GAAAGACGAACTG (SEQ ID NO: 8). The K13 fragment was generated using the method described in the aforementioned US Patent Publication with minor modifications, which is incorporated herein by reference in its entirety. Briefly, a polynucleotide encoding SalI site-KKDEL-RVELKDEL-stop codon-XhoI-EcoRI sequence was synthesized through serial polymerase chain reaction (PCR). The PCR-amplified DNA fragments were cleaved with Sal I and Eco R I and then purified by gel electrophoresis and electro-elution. The purified Sal I-Eco R I DNA fragments were ligated to pPE to form the plasmid pPE-K13.

pPE-DgD-K13. The plasmid encoding PE-DgD-K13 was generated using the method as described in U.S. patent application Ser. No. 10/457,574 with minor modifications. Briefly, two plasmids pET15-H6-PE(ΔIII) PRRS7-DgD and pPE-K13 were digested with PstI and XhoI to generate the fragment containing PE(ΔIII) PRRS7-DgD and the fragment containing the carboxyl terminal moiety, respectively. The two fragments were purified and then ligated by T4 ligase to form pET23-H6-PE(ΔIII)-DgD-K13 (named pPE-DGDK13 or pPE-DgD-K13). Plasmids pET23-K13, pET-K13, or pPE (ΔIII)-K13 all comprise the sequence KDEL.

pPE-ORF5-K13. The plasmid encoding PE-ORF5-K13 was generated according to the method as described previously. Briefly, PRRSV ORF5 gene was inserted into pPE (ΔIII)-K13 to construct pPE-ORF5-K13.

Fusion Antigen Expression and Purification. *E. coli* (BL21 (DE3)pLys cells) transformed with a fusion antigen plasmid for expression of a fusion protein PE-ORF5-K, PE-DgD-K13 or PE-M12-K13 were cultured in Luria Bertani broth containing ampicillin (100~500 ppm) at 37° C. After *E. coli* culture had reached an early log phase (A600=0.1~0.4), isopropyl-1-thio-β-D-galactopyranoside (IPTG) in a final concentration of 0.5 mM was added into the culture for induction. Cells were harvested 2 hours after the induction and immediately stored at −70° C. The fusion antigen was partially purified by urea extraction as described previously (Liao et al., 1995, Appl. Microbiol. Biotechnol. 43: 498-507). Under denaturing conditions, the fusion antigen molecules containing 6H is tag were fully exposed for improving binding to the eNi-NTA matrix (Ni-NTA agarose; Qiagen™ Inc. Calif.).

The efficiency of the purification was therefore maximized by reducing the potential for nonspecific binding. Batch purification of 6His-tagged fusion antigen from E. coli cell culture under denaturing conditions was described as follows.

One ml of 50% Ni-TNA slurry was added to 4 ml of lysate and mixed gently by shaking (e.g., 200 rpm) for 60 min at the room temperature to form a lysate-resin mixture. The lysate-resin mixture was carefully loaded into an empty column with the bottom cap still attached. The bottom cap was then removed to collect the flow-through solution. The column was washed twice with 4 ml of wash buffer (100 mM $NaH_2PO_4$, 10 mM Tris-HCl, 8 M urea, pH 8.0). The protein was eluted 4 times with 0.5 ml, pH 5.9 elution buffer (100 mM $NaH_2PO_4$, 10 mM Tris-HCl, 8M urea, pH 5.9) followed by 4 times of elution with 0.5 ml pH 4.5 elution buffer (100 mM NaH.sub.2PO.sub.4, 10 mM Tris-HCl, 8 M urea, pH 4.5). The collected fractions were pooled together and analyzed by SDS-PAGE gel electrophoresis. Quantitative analysis was performed using standard BSA protein.

TABLE 2

| Primer | SEQ ID NO: | Sequence |
|---|---|---|
| *M12-F1 | 10 | 5'-TGG CCG GTG GTG TCA ACC CAG AAC AAT GAA AAG TGG CCG GAT CGT CTG-3' |
| *M12-F2 | 11 | 5'-CAG TTT GCC AAA CTC CCA ATA GAA CTT GCA CCA CAC TGG CCG GTG GTG TCA-3' |
| M12-F3 | 12 | 5'-AAC TTG GGT TTT TAT TTT TCA CCT GAC TTG ACA CAG TTT GCC AAA CTC-3' |
| M12-F4 | 13 | 5'-GGG TCG AGC TCT CCG CTC CCG AAG GTC GCA CAC AAC TTG GGT TTT TAT-3' |
| M12-F5 | 14 | 5'-TCT CTC CGC GCC ATT TGT GCT GAT CTG GAA GGG TCG AGC TCT CCG-3' |
| M12-F6 | 15 | 5'-GAT AAA TTT CGT GCC ACA GAC AAG CGT GTT GTA GAT TCT CTC CGC GCC ATT-3' |
| M12-F7 | 16 | 5'-ACG GTT GCT CAG GCT CTG GGC AAC GGG GAT AAA TTT CGT GCC-3' |
| M12-F8 | 17 | 5'-CCC CCC GAC GTC AAT AAC AAA GAA TGC ACG GTT GCT CAG GCT-3' |
| M12-R1 | 18 | 5'-GCG GCT GTA TTT GTC GAG AGG GCG AAG GCT GGC AAC CAG ACG ATC CGG CCA-3' |
| M12-R2 | 19 | 5'-AGG GCC ACC CAT ATA GCC GGC ACC GAT GCA CGC GCG GCT GTA TTT GTC-3' |
| M12-R3 | 20 | 5'-GTA TGA CAC GAC CCC TGG AGT GCC CAG AAA CAC CGA AGG GCC CAC CAT ATA-3' |
| M12-R4 | 21 | 5'-AGC CTC GCC CTT AAC AAA CTT TGT GAG ATA GTA TGA CAC GAC CCC-3' |
| M12-R5 | 22 | 5'-TCG GCC GGT ACT GAA GAC CGT TCC GGG AAG CAC TTG AGC CTC GCC CTT AAC-3' |
| M12-R6 | 23 | 5'-G ATA TTC ACG GCA GTC TAC CTC AAT TCG GCC GGT ACT GAA-3' |
| M12-R7 | 24 | 5'-A CGC AGC AAC TTC TCG CTC ACG ATC ATC AAG ATA TTC ACG GCA GTC-3' |

TABLE 2-continued

| Primer | SEQ ID NO: | Sequence |
|---|---|---|
| M12-R8 | 25 | 5'-TTT TTT CTC GAG GAA TTC GTG TGG GAG GGA CGC AGC AAC TTC TCG-3' |

*:M12-F1 and M12-R1 denote the first pair of forward and reverse primers, respectively; M12-F2 and M12-R2 denote the second pair of forward and reverse primers, respectively, and so on.

Example 1

Induction of Cell Mediated Immune Responses by PRRSV Fusion Antigen

Figure 5:
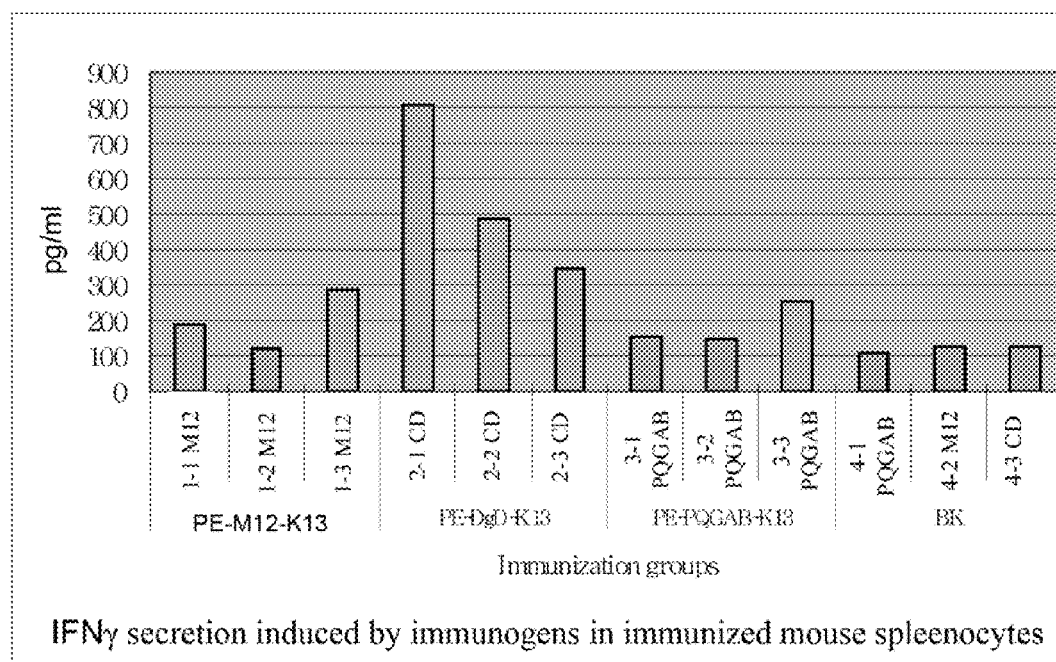
FIG. 5 illustrates the induction of antigen-specific IFNγ secretion in the spleenocytes of immunized mice by fusion antigens PE-M12-K13 and PE-DgD-K13.
Figure 6:
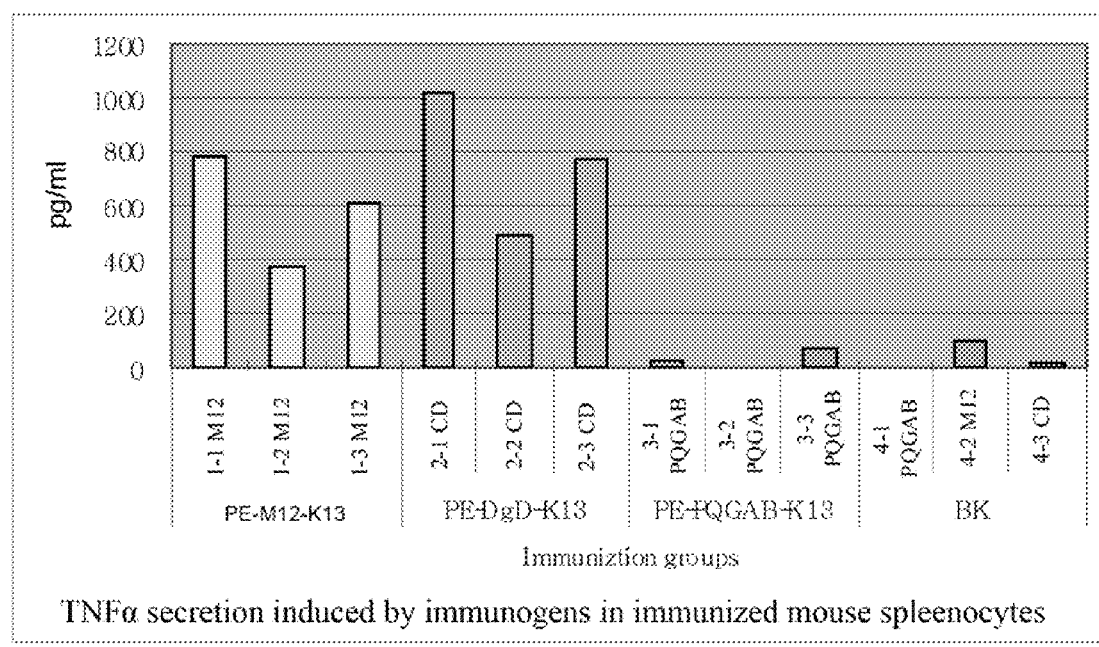
FIG. 6 illustrates the induction of antigen-specific TNFα secretion in the spleenocytes of immunized mice by fusion antigens PE-M12-K13 and PE-DgD-K13.

The focus of the invention was to discover those antigenic or epitopic regions in the PRRS virus proteins which have the characteristics of inducing a cell-mediated immune response in animals, and utilize those antigens to generate fusion antigens as vaccines for immunizing animals to induce the immune system to produce an enough quantity of IFNγ and TNFα, and activate T cell immunity and cytotoxic T cell pathway. The fusion antigens PE-DgD-K13 (or PE-PRRSV ORF7) and PE-M12-K13 were found capable of inducing cell mediated immune mechanisms. In the immunized mouse experimental model, the spleen cells were found to have induced cell immune mechanisms by PE-DgD-K13 and/or PE-M12-K13. Mice immunized with PE-M12-K13 and PE-DgD-K13, respectively, had increased secretions of IFNγ and TNFα compared with those of the control groups. The fusion antigen PE-PQGAB-K13, which comprised of ORF5 and ORF6 N-terminus-K13, had little effect in inducing IFNγ and TNFα secretions (FIGS. 5 and 6).

The ORF1b gene plays an important role in virus replication before the proliferation. Fusion antigens PE-DgD-K13 or PE-DgD-K3 and PE-M12-K13 or PE-M12-K3 will be the most important main ingredients for PRRSV vaccines.

According to the PRRSV challenge studies and blood sample test previously, PE-DgD-K3 was found capable of activating piglet immune protections, preventing piglets from inflicting viremia.

Example 2

Dosages of PRRS Fusion Antigens

One milligram of antigen(s) was administered to piglets at the age of one, two, or 5 weeks, with a total of 3 times of immunization. Two weeks after the last immunization, specific antibodies IgG, IgA, and IgM titers were measured. It was found that the antibody titer could reach a peak after twice immunizations. The antibody titer after three times immunizations did not show much difference from that of twice immunizations.

When piglets were given 0.05~0.5 mg, but preferred in 0.1~0.3 mg, of a vaccine composition comprising a fusion antigen PE-M12-K13, a sufficient antibody reaction was induced after the second time immunization, and the antibody reached a peak after the third time immunization.

Example 3

Protection Against PRRS Virus Challenge by Vaccine Composition in a Mixture Formulation of PE-M12-K13 and Other Fusion Antigen(s)

Animals. Pigs were obtained from a herd in the SPF farm that was periodically tested for PRRSV and known to be free of the virus by RT-PCR. Before the experiments, the SPF farm sows were confirmed free of viremia. In addition, an Index-RRRS diagnostic reagent test also showed negative results in the SPF sows.

RNA Extraction. To detect the presence of PRRSV in animals, blood plasma fractions were collected and RNAs extracted with a NUCLEOSPIN RNA II™ kit for RT-PCR. (Macherey-Nagel GmbH & Co. KG, Germany). Briefly, three hundred and fifty microliters of RA1 solution and 3.5 µl of β-mercapto-ethanol were added into 100 µl of plasma fraction. After the viscosity was reduced and the lysate cleared by filtration, the lysate was mixed with 350 µl of 70% ethanol. The RNA was adsorbed into a Nucleospin™ RNA column by centrifugation and followed by wash. Ninety-five microliters of DNase solution were applied into the column for DNA digestion. After repeating wash and centrifugation for several times, RNA was eluted by 60 µl of RNase-free water.

RT-PCR Detection of Virus. RT-PCR was performed by using an Onestep RT-PCR Kit™ (Qiagen® Inc. Calif.) to detect the presence of PRRSV RNA in animals. The forward primer 5'-CCA GCC AGT CAA TCA GCT GTG-3' (SEQ ID NO: 3) and the reverse primer 5'-GCG GAT CAG GCG CAC-3' (SEQ ID NO: 4) were provided for synthesizing a 293-bp fragment. The detection limit of RT-PCR by agarose gel electrophoresis was around 10 copies of PRRSV ($TCID_{50}$/ml).

Immunization. New-born piglets were selected from 3~4 sows in SPF farm and individually identified, weighed, and sex determined. Piglets were randomly divided into 6 groups with each group comprised of five or six piglets from each sow. The piglets were vaccinated with a vaccine composition comprising one or more than one fusion antigen (i.e., with or without combination), or vehicle on the basis of weight stratification. Immunization was performed twice at suckling stage at age of 4 and 18 days by an intramuscular injection with 2 ml of a vaccine composition containing 1 ml of fusion antigen(s) (50~100 µg each antigen component/dose) emulsified in 1 ml ISA206 (SEPPIC®, France), respectively. The control group was raised without immunization. At the weaning stage (approximately 3~4 weeks of age), each group was moved into individual isolation rooms equipped with air conditioning and ventilation.

PRRSV Challenge. Two weeks after the last vaccination, piglets were intranasally challenged by PRRSV after being sedated with Ketamine (100 mg, IM injection) and cough-reflex suppressed with 2% Lidocaine (1 ml, intranasal instillation). One ml of inocula containing $1 \times 10^7$ 50% tissue culture infected doses ($TCID_{50}$) per ml of fresh MD-1 strain of PRRSV was administered by intranasal route. Five piglets were challenged in each group.

RT-PCR Post Virus Challenge. To detect the level of PRRSV in blood after the virus challenge, the blood leukocyte samples (the isolated the puffy cord layer from whole blood) of the piglets were assayed with RT-PCR two weeks after the second immunization. The blood leukocyte samples of the piglets were again assayed with RT-PCR for detection of PRRSV on 3, 7, and 14 days after the challenge.

Result. Prior to the virus challenge, all piglets showed negative in the RT-PCR blood sample test for PPRSV. Thus, no viremia occurred in the control group prior to the PRRSV challenge. Five days post PPRSV challenge (DPI-5), piglets in the control group started to show viremia in the blood samples. About 2 weeks after the PRRSV challenge, all piglets in the control group showed viremia (Table 2, 5 out of 5 in BK-1; 6 out of 6 in BK-2). The viremia was detectable for a long time. Whether the piglets' blood samples had viremia two weeks after the PRRSV challenge was an important index for evaluation of the efficacy of the vaccine. The absence of viremia would indicate that the vaccine had exerted its efficacy. In particular, the group vaccinated with the vaccine composition containing a mixture of PE-M12-K13, PE-ORF5-K13 and PE-DgD-K13 had only 1 out of 6 pigs was tested PRRSV positive in the blood sample. Some vaccinated groups with PE-M12-K13 started to show viremia clearance reaction on day 14 post virus challenge (DPI-14), as shown in Table 2.

Table 2 shows the result of post PPRSV challenge for animal groups. Piglets vaccinated with PE-M12-K13 had one out of 3 showed viremia on day-7 after the PRRSV challenge, but the viremia was cleared by day-21 post the challenge. The composition as a mixture of PE-M12-K13, PE-DgD-K13 and PE-ORF5-K13 had one of 6 showed viremia on day-7 post the challenge, and the viremia cleared by day-21 after the challenge. It was likely that PE-DgD-K13 (or -K3) and PE-M12-K13 (or -K3) were effective in protecting the animals, but PE-ORF5-K13 (or -K3) did not afford an additional protection in this circumstance.

TABLE 2

Results of Viremia Test after PPRSV Challenge in SPF Piglet Model

| Experiment No. | Vaccine Composition | No. of Piglets | DPI-2 | DPI-7 | DPI-14 | DPI-21 |
|---|---|---|---|---|---|---|
| No. 1 | *BK-1 | 5 | 1 | 3 | 5 | 2 |
| No. 1 | PE-M12-K13 | 5 | 2 | 1 | 1 | 0 |
| No. 2 | BK-2 | 6 | 1 | 3 | 6 | 4 |
| No. 2 | PE-DgD-K13, PE-M12-K13, PE-ORF5-K13 | 6 | 0 | 1 | 1 | 0 |

The term *"BK" represents the non-vaccinated control group.

Example 4

Pulmonary Pathogenesis by PPRSV Challenge

The statistics significance in the difference of the interstitial pneumonia index between the vaccinated and non-vaccinated animal groups was determined by ANOVA test. The statistics analysis showed that animals vaccinated with the vaccine composition formulated with one single PE-PRRSV fusion protein PE-M12-K13 showed a light degree of interstitial pneumonia seriousness in the lung tissue section.

With respect to the vaccine compositions that included more than one single PRRSV fusion antigen, the studies on the vaccine composition comprising a mixture of PE-DgD-K13 and PE-M12-K13 showed it could afford an effective protection from the pulmonary symptoms. The lung tissue sections from PE-DgD-K13 and PE-M12-K13-vaccinated piglets showed less serious degree of interstitial pneumonia.

In conclusion, the vaccine composition that comprises PE-M12-K13 has been demonstrated to have the following features:

I. Having an effective viremia-clearance reaction.
II. The vaccine composition that contained no other PRRSV structural protein was effective in reducing side effects that might be induced by the PRRS virus.
III. Ability to induce cellular immune mechanisms. By utilizing ORF1b, fusion protein antigen PE-M12-K13 was generated and showed efficacy in inducing animals to produce cytokine INFγ and TNFα, which were effective in clearing viral infection.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A fusion antigen specific for a target cell comprising:
   a) an antigenic moiety;
   b) a ligand moiety which is capable of reacting, recognizing or binding to a receptor on the target cell;
   c) a *Pseudomonas* exotoxin A translocation domain II; and
   d) a carboxyl terminal moiety comprising a polypeptide having the amino acid sequence of KKDELRVELKDEL (SEQ ID NO: 7).

2. A fusion antigen specific for a target cell comprising:
   a) an antigenic moiety comprising a polypeptide that is the translation product of a DNA fragment having the nucleotide sequence of SEQ ID NO: 2;
   b) a ligand moiety capable of reacting, recognizing or binding to a receptor on the target cell;
   c) a *Pseudomonas* exotoxin A translocation domain II; and
   d) a carboxyl terminal moiety comprising a polypeptide having the amino acid sequence of KKDLRDELKDEL (SEQ ID NO: 5) or KKDELRDELKDEL (SEQ ID NO: 6).

3. The fusion antigen of claim 1, wherein the antigenic moiety is derived from porcine reproductive and respiratory syndrome virus (PRRSV) ORF1b or ORF7.

4. The fusion antigen of claim 1, wherein the antigenic moiety is derived from PRRSV Nsp10 and Nsp11.

5. The fusion antigen of claim 1, wherein the antigenic moiety is derived from PRRSV ORF1b.

6. A fusion antigen specific for a target cell comprising:
   a) an antigenic moiety comprising a polypeptide having the amino acid sequence of SEQ ID NO: 1;
   b) a ligand moiety capable of reacting, recognizing or binding to a receptor on the target cell;
   c) a *Pseudomonas* exotoxin A translocation domain II; and
   d) a carboxyl terminal moiety comprising a polypeptide having the amino acid sequence of KDEL (SEQ ID NO: 9).

7. The fusion antigen of claim 1, wherein the antigenic moiety comprising a polypeptide that is the translation product of a DNA fragment having the nucleotide sequence of SEQ ID NO: 2.

8. The fusion antigen of claim 1, wherein the antigenic moiety is derived from a PRRSV protein.

9. A pharmaceutical composition comprising at least one fusion antigen according to claim 3.

10. The fusion antigen of claim 2, wherein the antigenic moiety is derived from PRRSV ORF1b or ORF7.

11. The fusion antigen of claim 1, wherein the antigenic moiety is derived from PRRSV Nsp10 and Nsp11.

12. The fusion antigen of claim 1, wherein the antigenic moiety is derived from PRRSV ORF1b.

13. The fusion antigen of claim 6, wherein the carboxyl terminal moiety comprises the amino acid sequence of KKDELRDELKDEL(SEQ ID NO: 6) or KKDELRVELKDEL (SEQ ID NO: 7).

14. A pharmaceutical composition comprising at least one fusion antigen according to claim 13 and a pharmaceutically acceptable carrier.

15. The fusion antigen of claim 2, wherein the antigenic moiety is derived from a PRRSV protein.

16. A pharmaceutical composition comprising at least one fusion antigen according to claim 11.

17. The fusion antigen of claim 1, wherein the carboxyl terminal moiety is connected to the antigenic moiety via a bridge region.

18. The fusion antigen of claim 1, wherein the ligand moiety is a *Pseudomonas* exotoxin A binding domain I.

19. A pharmaceutical composition comprising one or more than one fusion antigen according to claim 1 and a pharmaceutically acceptable carrier.

20. The pharmaceutical composition of claim 19 comprising at least one fusion antigen having an antigenic moiety derived from PRRSV ORF1.

21. The pharmaceutical composition of claim 20 comprising at least one fusion antigen having an antigenic moiety derived from PRRSV ORF7.

22. The pharmaceutical composition of claim 19 comprising at least one fusion antigen having an antigenic moiety derived from PRRSV ORF7.

23. A pharmaceutical composition comprising one or more than one fusion antigen according to claim 2 and a pharmaceutically acceptable carrier.

24. The pharmaceutical composition of claim 19 comprising more than one fusion antigen, in which at least one fusion antigen comprises an antigenic moiety derived from PRRSV ORF1b.

25. The pharmaceutical composition of claim 19 comprising more than one fusion antigen, in which at least one fusion antigen comprises an antigenic moiety derived from PRRSV ORF7.

26. A method of inducing an immune response in an animal against a pathogen infection comprising the steps of:
   a) providing a pharmaceutical composition according to claim 19; and
   b) inoculating the composition comprising the fusion antigen into the animal, wherein the immune response is directed against the pathogen from which the antigen moiety is derived.

27. A method of inducing an immune response in an animal against a pathogen infection comprising the steps of:
   a) providing a pharmaceutical composition according to claim 20; and
   b) inoculating the composition comprising the fusion antigen into the animal, wherein the immune response is directed against the pathogen from which the antigen moiety is derived.

28. A method of inducing an immune response in an animal against a pathogen infection comprising the steps of:
   a) providing a pharmaceutical composition according to claim 21; and
   b) inoculating the composition comprising the fusion antigen into the animal, wherein the immune response is directed against the pathogen from which the antigen moiety is derived.

29. A method of inducing an immune response in an animal against a pathogen infection comprising the steps of:
   a) providing a pharmaceutical composition according to claim 23; and
   b) inoculating the composition comprising the fusion antigen into the animal, wherein the immune response is directed against the pathogen from which the antigen moiety is derived.

30. A method of inducing an immune response in an animal against a pathogen infection comprising the steps of:
   a) providing a pharmaceutical composition comprising a fusion antigen according to claim 6; and
   b) inoculating the composition comprising the fusion antigen into the animal, wherein the immune response is directed against the pathogen from which the antigen moiety is derived.

31. A method of inducing an immune response in an animal against a pathogen infection comprising the steps of:
   a) providing a pharmaceutical composition comprising a fusion antigen according to claim 13; and
   b) inoculating the composition comprising the fusion antigen into the animal, wherein the immune response is directed against the pathogen from which the antigen moiety is derived.

32. The method of claim 26, wherein the pathogen is a porcine reproductive and respiratory syndrome virus.

33. The method of claim 29, wherein the pathogen is a porcine reproductive and respiratory syndrome virus.

34. The method of claim 30, wherein the pathogen is a porcine reproductive and respiratory syndrome virus.

35. The method of claim 29, wherein the target cell is an antigen presenting cell.

36. The method of claim 30, wherein the target cell is selected from the group consisting of T-cells, B-cells, dendritic cells, monocytes, and macrophages.

37. The pharmaceutical composition of claim 16, wherein the at least one fusion antigen comprises an antigen moiety derived from PRRSV ORF7.

38. The pharmaceutical composition of claim 9, wherein the at least one fusion antigen comprises an antigen moiety derived from PRRSV ORF7.

39. A pharmaceutical composition comprising at least one fusion antigen according to claim 6 and a pharmaceutical carrier.

40. The pharmaceutical composition comprising at least one fusion antigen according to claim 13 and a pharmaceutical carrier.

41. The phrmaceutical composition of claim 40 further comprising a second fusion antigen specific for a target cell, the second fusion antigen comprising:
   a) an antigenic moiety derived from PRRSV ORF7;
   b) a ligand moiety which is capable of reacting, recognizing or binding to a receptor on a target cell;
   c) a *Pseudomonas* exotoxin A translocation domain II; and
   d) a carboxyl terminal moiety comprising a polypeptide having the amino acid sequence of KDEL (SEQ ID NO: 9).

42. The pharmaceutical composition of claim 39 further comprising a second fusion antigen specific for a target cell, the second fusion antigen comprising:
   a) an antigenic moiety derived from PRRSV ORF7;
   b) a ligand moiety which is capable of reacting, recognizing or binding to a receptor on a target cell;
   c) a *Pseudomonas* exotoxin A translocation domain II; and
   d) a carboxyl terminal moiety comprising a polypeptide having the amino acid sequence of KDEL (SEQ ID NO: 9).

\* \* \* \* \*